United States Patent [19]

Siegman

[11] Patent Number: 4,910,353

[45] Date of Patent: Mar. 20, 1990

[54] DEHALOGENATION OF POLYCHLORINATED BIPHENYLS AND OTHER RELATED COMPOUNDS

[75] Inventor: John R. Siegman, Cuyahoga Falls, Ohio

[73] Assignee: Transformer Service, Inc., Akron, Ohio

[21] Appl. No.: 609,229

[22] Filed: May 11, 1984

Related U.S. Application Data

[63] Continuation of Ser. No. 464,475, Feb. 7, 1983, abandoned.

[51] Int. Cl.[4] .............................................. C07C 25/08

[52] U.S. Cl. ...................................................... 570/204

[58] Field of Search ........................... 549/67; 570/204

[56] References Cited

PUBLICATIONS

Bunnett et al. (Bunnett), *J. Am. Chem.* Soc., 90:810-811 (1968).

Nelson et al. (Nelson), *J. Org. Chem.*, 39:1425 (1974).

Feiser & Feiser Reagents for Org. Synth. vol. 2 (1969) p. 158.

Crown Zellerbach Corp. Dimethyl Sulfoxide Tech Bulletin (1988) pp. 5, 7.

*Primary Examiner*—Alan Siegel

*Attorney, Agent, or Firm*—Oldham & Oldham Co.

[57] ABSTRACT

Polychlorobiphenyls and other toxic halogenated polyaromatic substances such as various halogenated pesticides, herbicides, and the like, are dehalogenated through the use of a strong base and various sulfur-containing compounds. The dechlorinated residues either form polymers which are insoluble in aliphatic hydrocarbons and can thus be easily separated as through filtration, or can be separated from the solvent by distillation. The residues can be readily and safely disposed of as in an approved dump, or burned.

1 Claim, No Drawings

DEHALOGENATION OF POLYCHLORINATED BIPHENYLS AND OTHER RELATED COMPOUNDS

This is a continuation of application Ser. No. 464,475, filed Feb. 7, 1983, now abandoned.

TECHNICAL FIELD

The present invention relates to the dehalogenation of various toxicants such as polychlorinated biphenyls and other halogenated polyaromatic compounds such as herbicides, pesticides, and the like. More specifically, the present invention relates to the use of a strong base as well as various sulfur-containing compound to dehalogenate said toxicants.

BACKGROUND ART

Heretofore, very little has been accomplished with regard to detoxifying various compounds such as polychlorinated biphenyls. Generally, the standard procedure was to place the various toxicants in a barrel and bury it at some EPA approved dump site. Of course, this does not solve the problem in that once the barrels rust through, the toxicants will contaminate the surrounding earth.

An article bearing the title "The Base-Catalyzed Halogen Dance, and Other Reactions of Aryl Halides," by Joseph Bunnett, Accounts of Chemical Research, Vol. 5, 1972, page 139–147, relates to various aryl halide reactions. However, this article specifically states that dechlorination of aryl halides, though sought, did not occur, page 141. This article is not pertinent in that it totally fails to teach or suggest any dechlorination or dehalogenation of biphenyl type compounds, detoxification of various halogenated polyaromatic compounds, and the like. Furthermore, it fails to teach any suggestion of a formation of a polymer from a toxicant.

A German article published in Zeitschrift Fur Chemie, 1969, at page 141, relates to preparing methyl substituted toluene. It thus fails to teach any detoxification or dehalogenation of various types of polyaromatic halogenated compounds such as polychlorinated biphenyls, the formation of a polymer from the toxicants, and the like.

An article by Corey and Chaykovsky relating to "Methylsulfinyl Carbanion ($CH_3$—SO—$CH_2^-$), Formation and Applications to Organic Synthesis," published in the Journal of the American Chemical Society, Mar. 20, 1965, pages 1345–1349, also teaches the methylation of benzene compounds. It is thus not pertinent in that it fails to teach any dehalogenation or detoxification of various toxicants such as polychlorinated biphenyls, halogenated polyaromatic compounds, and the like. No suggeston is further made of any polymer formation from the detoxified compound.

DISCLOSURE OF INVENTION

It is therefore an aspect of the present invention to detoxify various toxicants.

It is yet another aspect of the present invention to detoxify various toxicants, as above, such as to dechlorinate various polychlorinated biphenyls.

It is a further aspect of the present invention to detoxify various toxicants, as above, wherein said toxicants include halogenated polyaromatic pesticides and herbicides.

It is a further aspect of the present invention to detoxify various toxicants, as above, wherein a strong base and various sulfur compounds are utilized.

It is yet another aspect of the present invention to detoxify various toxicants, as above, wherein a polymer is formed from the toxicant and can be readily separated from the reaction medium.

It is yet another aspect of the present invention to detoxify various toxicants, as above, wherein high concentrations of polychlorinated biphenyls, for example, 10,000 to 20,000 parts per million, can be detoxified to levels of less than two parts per million.

It is yet another aspect of the present invention to detoxify various toxicants, as above, wherein said reaction is readily carried out, is economical, and requires a modicum amount of time.

These and other aspects of the present invention will become apparent from the following detailed disclosure thereof.

In general, a dehalogenated halogen-containing toxicant, comprises: the dehalogenated toxicant being the reaction product of the halogen-containing toxicant, a strong base, and a sulfur-containing compound; said toxicant selected from the group consisting of polychlorinated biphenyl, a halogenated polyaromatic herbicide, a halogenated polyaromatic pesticide, and combinations thereof; said sulfur-containing compound selected from the group consisting of (a) a sulfoxide compound having the formula

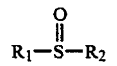

where $R_1$ and $R_2$ are the same or different, where $R_1$ and $R_2$ are an alkyl group having from 1 to 20 carbon atoms, a phenyl group, or an alkyl substituted aromatic having from 7 to 12 carbon atoms, (b) a sulfone having the formula

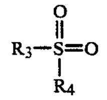

where $R_3$ and $R_4$ can be the same or different, where $R_3$ and $R_4$ are an alkyl having from 1 to 20 carbon atoms, (c) a sulfolane having the formula

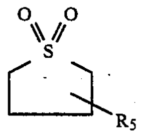

where $R_5$ is an alkyl having from 0 to 10 carbon atoms, and (d) combinations thereof, and wherein said reaction is carried out at a temperature of from about ambient to about 200° C.

In general, a process for the dehalogenation of a halogen-containing toxicant, comprising the steps of: contacting and reacting the halogen-containing toxicant with a strong base and a sulfur-containing compound, said toxicant selected from the group consisting of polychlorinated biphenyl, a halogenated polyaromatic herbicide, a halogenated pesticide, and combinations thereof, the amount of said strong base and said sulfur-containing compound ranging from about 20 to about 100 equivalents for each halogen atom in said toxicant, said sulfur compound selected from the group consisting of (a) a sulfoxide compound having the formula

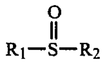

where $R_1$ and $R_2$ are the same or different, where $R_1$ and $R_2$ are an alkyl group having from 1 to 20 carbon atoms, a phenyl group, or an alkyl substituted aromatic having from 7 to 12 carbon atoms, (b) a sulfone having the formula

where $R_3$ and $R_4$ can be the same or different, where $R_3$ and $R_4$ are an alkyl having from 1 to 20 carbon atoms, (c) a sulfolane having the formula

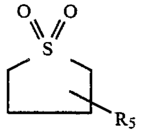

where $R_5$ is an alkyl having from 0 to 10 carbon atoms, and (d) combinations thereof.

BEST MODE FOR CARRYING OUT THE INVENTION

According to the concepts of the present invention, various toxicants are detoxified, that is rendered harmless to the environment. One class of toxicants are the so-called polychlorinated biphenyls, that is PCB. Such compounds are generally biphenyl groups containing from 1 to 10 chlorine atoms thereon. Such chlorinated biphenyls have lately come under close scrutiny to various environmental agencies as being harmful to the environment and stringent requirements have been set on the use and disposal thereof.

Another group of compounds which are detoxified include halogenated polyaromatic herbicides and pesticides. These compounds have various aromatic structures with halogen groups thereon, for example, chlorine, and are well known to the art.

An important aspect of the present invention is the use of a strong base. An example of a strong base is an alkali hydride, such as sodium hydride or lithium hydride. Another group of bases is the alkali metal alkoxides, wherein the alkali group has from 1 to 10 carbon atoms. Of the various alkali metals, sodium is preferred. Specific examples of such compounds include sodium isopropoxide which is a preferred compound, sodium t-butoxide, also preferred, sodium methoxide, and the like. Another group is the alkali hydroxide compounds such as sodium hydroxide, potassium hydroxide, and the like. Another suitable base is the alkali amides such as sodium amide or potassium amide. The alkali metals can also be used such as sodium, potassium, or lithium. Still another group includes the alkyl lithium compounds having from 1 to 8 carbon atoms such as methyl lithium, butyl lithium, and the like. The aromatic lithium compounds and the alkyl substituted aromatic lithium compounds having from 6 to 12 carbon atoms can also be used. A strong base is utilized to generally promote a chemical reaction and shift the equilibrium of the reaction.

The amount of the base utilized is in direct proportion to the amount of chlorination contained by the various compounds. Generally, a quick determination can be made of the solutions, material, or composition being treated as a gas chromatographic analysis. The molar excess of base utilized per chlorine atom contained by the various compounds or the equivalent excess of base utilized generally ranges from about 10 to about 100 equivalents, desirably from 10 to 20 equivalents, and preferably from about 14 to about 16 equivalents. Usually, anything less than 10 equivalents does not result in sufficient detoxification. On the other hand, large amounts of equivalents, although reducing the time, tend to be exceedingly costly. Generally, it has been found that the use of from about 14 to about 16 equivalents produces the desired detoxification.

The toxicant material, when treated with the base, is carried out at a temperature ranging from about ambient temperature, that is from about 15° C. to about 200° C. A range of from about 50° C. to about 150° C. is desired, with the temperature of from about 65° C. to about 100° C. being preferred. Generally, the overall reaction at ambient temperatures will take approximately 24 hours to complete. However, at temperatures in excess of 50° to 65° C., the reaction time is reduced to approximately two hours. Desirably, the reaction is carried out in an inert atmosphere such as nitrogen, argon, and the like.

A sulfur-containing compound is also utilized in the detoxification reaction of the various toxicants. One group of such sulfur-containing compounds includes compositions having the formulation

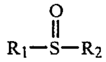

where $R_1$ and $R_2$ can be the same or different, where R is an alkyl group having from 1 to 20 carbon atoms, or desirably from 1 to 10 carbon atoms, a phenyl group, an alkyl substituted phenyl having from 7 to 12 carbon atoms, and can be part of a cyclic ring, e.g., tetramethylene sulfoxide. When R is a phenyl group, only one of the "R" groups is phenyl. Preferably, $R_1$ and $R_2$ are methyl and hence dimethyl sulfoxide is a preferred compound. Another group of sulfur-containing compounds are the sulfones, that is compounds having the formula

where $R_3$ and $R_4$ can be the same or different, and can be an alkyl group containing from 1 to 20 carbon atoms, or desirably from 1 to 10 carbon atoms. Of the various sulfone compounds, dimethyl sulfone is preferred. Still another sulfur-containing compound is the sulfolanes, that is compounds of the formula

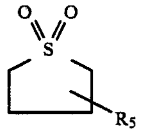

where $R_5$ is an alkyl having from 0 to 10 carbon atoms, and desirably from 0 to 6 carbon atoms. Sulfolane is preferred.

Of the various sulfur compounds, tetramethylene sulfoxide, sulfolane, dimethylsulfone, and dimethyl sulfoxide are preferred.

The amount of sulfur-containing compound utilized is generally the same as the amount of the base. That is, from about 10 to about 100 equivalents for each chlorine atom, desirably from about 10 to about 20, and preferably from about 14 to 16 is utilized. The reaction temperature between the sulfur-containing compound and the toxicant is the same as for the base, that is as from about ambient to 15° C. to about 200° C., desirably from about 50° C. to about 150° C., and preferably from about 65° C. to about 100° C.

The base can be added first to the toxicant. Then the sulfur-containing compound can be added. Alternatively, both the strong base and the sulfur-containing compounds can be added simultaneously to the toxicant. The reaction time, as noted above, will generally vary with the temperature. The reaction time is generally such that the amount of PCB remaining is less than 2 parts per million. Generally, the reaction is carried out at temperatures in excess of 65° C. and the reaction time is on the order of approximately two to three hours.

The reaction mechanism is not clearly understood. However, it is known that the reaction between the base and the sulfur compounds with the toxicants removes the halogen or chlorine atom from the compound to detoxify it. The chlorine atom or radical is then generally tied up in the form of a salt, for example sodium chloride. Additionally, the toxicant is often polymerized during the reaction. Such polymers are readily separated out from the solutions since they are generally insoluble in various aliphatic hydrocarbons. The separation can be accomplished utilizing any conventional filtration method or separator. If not formed as a polymer, the toxicant residue will usually exist in a solvent. If not, the residue can be added to a solvent. The solvent can be readily removed as through distillation. The polymers so separated can either be dumped as in a certified EPA dump, or burned.

According to the present invention, it has been found that contaminated material having in excess of 10,000 to 20,000 parts per million of contaminated material can be readily reduced to a contaminate level of less than 2 parts per million. Moreover, as apparent from above, the process is readily carried out by using mild heat and fairly short reaction time periods. The end product is generally a harmless polymer, or solid material, which can be burned if desired. Alternatively, the residue or polymer can be used as a by-product.

One specific area in which the present invention can be utilized is in the treatment of transformer oils having polychlorinated biphenyls therein. According to the present invention, such transformer oil can be readily treated, and recycled and once again used in the transformer. Other areas of use include waste oils and transformer flushing solvents such as kerosene and the like. Still others include the detoxification of pesticides and herbicides.

The invention will be better understood by reference to the following examples.

EXAMPLE 1

Polychlorinated biphenyl (PCB) contaminated oil, in an amount of 50 cc (1500 ppm contamination), and 10 grams of 60 percent sodium hydride were placed in a nitrogen purged vessel. To the stirred mixture was added 1.1 cc of dimethyl sulfoxide (DMSO) while maintaining the nitrogen atmosphere at ambient temperature. After 30 minutes, an additional 1.1 cc of DMSO was added and stirring continued for an additional 20.5 hours.

Filtration of the mixture produced a clear oil containing 23 ppm PCB's.

EXAMPLE 2

PCB contaminated oil, in an amount of 50 cc (1500 ppm contamination) and 5.0 grams of 60 percent sodium hydride dispersion were placed in a vessel equipped with a mechanical stirrer and a nitrogen inlet. The vessel was placed in an oil bath at 65° C. and stirring and nitrogen purge commenced. When the internal temperature reached 65° C., 4 cc of DMSO were added over a 15 minute period and stirring continued for an additional 1.75 hours.

Filtration of the mixture yielded a clear oil containing less than 1 ppm PCB's.

EXAMPLE 3

PCB contaminated oil, in an amount of 50 cc (1890 ppm contamination) and 5 grams of 60 percent NaH were placed in a nitrogen purged vessel and heated to 150° C. under agitation. Two cc of DMSO were added over 5 minutes and the reaction continued for two hours.

Filtration of the mixture yielded a clear oil with no detectable amount of PCB's.

EXAMPLE 4

PCB contaminated oil, in an amount of 50 cc (PCB=1890 ppm contamination) and 5 grams of 60 percent NaH were placed in a vessel and heated to 85° C. with stirring under a nitrogen atmosphere. Two cc of tetramethylene sulfoxide were added and allowed to react for two hours.

Filtration of the mixture yielded a clear oil with no detectable level of PCB's.

EXAMPLE 5

PCB contaminated oil, in an amount of 50 cc (1500 ppm contamination) and 5 cc of sulfolane (tetrahydrothiophene-1,1-dioxide) were placed in a vessel fitted with a nitrogen inlet and a mechanical stirrer. The vessel was placed in an oil bath at 70° C. and nitrogen flow and stirring commenced. When the internal temperature reached 48° C., 1.0 gram of 60 percent sodium hydride dispersion (NaH) was added. After one hour (internal temperature 70° C.), an additional 1.0 gram of 60 percent NaH was added and stirring continued for an additional 6.25 hours.

Filtration of the mixture yielded a clear oil containing less than 1 ppm PCB's.

EXAMPLE 6

Mineral oil (100 cc) containing 1500 ppm PCB's was placed in a nitrogen purged vessel. Two grams of finely divided sodium and 4 cc of dimethyl sulfoxide were added and the mixture stirred at room temperature. An additional 4 cc of dimethyl sulfoxide were added and stirring continued for an additional 20 hours.

Filtration of the mixture produced a clear light colored oil that contained no detectable PCB's.

EXAMPLE 7

Sodium t-butoxide was prepared by reacting 1.0 gram of 60 percent sodium hydride with 2.0 gram t-butyl alcohol in 15 cc PCB contaminated oil in a nitrogen purged vessel for two hours at 43° C. After two hours, an additional 35 cc of PCB contaminated oil (1500 ppm) were added and the mixture heated to 43° C. 5.0 cc of dimethyl sulfoxide were added and the mixture stirred for 18 hours.

Filtration produced a clear oil containing less than 10 ppm PCB's.

EXAMPLE 8

To a nitrogen purged flask equipped with a magnetic stirrer was charged 1.0 gram of 60 percent NaH dispersion in oil and 10 cc hexane. After several minutes of mixing, the hexane was decanted and 10 cc of dimethylsulfoxide were added. The flask was placed in an oil bath at 60° C. and stirred until hydrogen evolution ceased, about two hours.

50 cc of transformer oil contaminated with 2000 ppm PCB's were heated to 80° C. and added to the contents of the flask. Five minutes of agitation followed by later separation and filtration yielded a clear oil with no detectable PCB's.

While in accordance with the patent statutes, a preferred embodiment and best mode have been described in detail, the scope of the invention is measured by the scope of the attached claims.

What is claimed is:

1. A process for the dehalogenation of a polychlorinated biphenyl comprising the steps of:

contacting and reacting the polycholorinated biphenyl with a strong base and a sulfur containing compound at a reaction temperature range, the amount of said strong base and said sulfur-containing compound ranging from about 10 to about 100 equivalents for each halogen atom in said polychlorinated biphenyl, wherein said sulfur containing compound is selected from the group consisting of dimethyl sulfoxide, tetramethylene sulfoxide, dimethyl sulfone, sulfolane, and combinations thereof, said strong base is selected from the group consisting of sodium hydride, lithium hydride, sodium t-butoxide, sodium isopropoxide, sodium hydroxide, potassium hydroxide, potassium amide, sodium amide, butyl lithium, methyl lithium, sodium, potassium, lithium, and combinations thereof, and wherein said reaction temperature range is from about 65° C. to about 100° C.

* * * * *